United States Patent [19]

Bartnik et al.

[11] Patent Number: 4,518,697

[45] Date of Patent: May 21, 1985

[54] ACID STABLE PROTEASE FROM MUTANTS OF GENUS ASPERGILLUS

[75] Inventors: Friedhelm Bartnik, Düsseldorf; Joachim Schindler, Hilden; Albrecht Weiss, Erkrath; Rolf Schmid, Düsseldorf, all of Fed. Rep. of Germany

[73] Assignee: Henkel Kommanditgesellschaft auf Aktien, Düsseldorf, Fed. Rep. of Germany

[21] Appl. No.: 449,415

[22] Filed: Dec. 13, 1982

[30] Foreign Application Priority Data

Dec. 14, 1981 [DE] Fed. Rep. of Germany ....... 3149457

[51] Int. Cl.³ .......................... C12N 1/14; C12N 9/62; C12R 1/685

[52] U.S. Cl. ................................. 435/254; 435/172.1; 435/225; 435/917; 426/63

[58] Field of Search ........................................ 435/254

[56] References Cited

U.S. PATENT DOCUMENTS 3,149,051  9/1964  Yoshida et al. ..................... 435/225
3,492,204  1/1970  Koaze et al. ........................ 435/235

*Primary Examiner*—Lionel M. Shapiro
*Attorney, Agent, or Firm*—Ernest G. Szoke; Henry E. Millson, Jr.; Mark A. Greenfield

[57] ABSTRACT

Process for the preparation of acid stable protease having a broad activity spectrum in high yields from mutants of the fungus Aspergillus, and the mutants used therein.

1 Claim, No Drawings

ACID STABLE PROTEASE FROM MUTANTS OF GENUS ASPERGILLUS

BACKGROUND OF THE INVENTION

This invention relates to a process for producing acid stable proteases having a broad pH activity spectrum in high yield from mutants of the genus Aspergillus, and to the new mutants used in the process.

It is known that acid stable proteases can be produced from the genus Aspergillus, as well as mutants thereof, which permit production of these proteases on an industrial scale.

DESCRIPTION OF THE INVENTION

The present invention has as its object the production of acid stable protease in yields exceeding those known to the art. This object has been accomplished by the mutation of selected wild strains of the Aspergillus genus, and selection of those mutants that exhibit enhanced protease forming capabilities.

In accordance with the invention, there are used wild strains of the genus Aspergillus, preferably of *Aspergillus niger* var. tienhem CBS 319.81 isolated from samples of earth. This latter strain forms an extracellular acid stable protease which is effective over a broad pH range. Mutation of the wild strains is carried out, preferably by the us of UV irradiation. The mutation treatment of the selected strains is repeated one or more times, as required.

The object of the invention accordingly is achieved by the discovery of a process for producing an acid stable protease with a broad pH activity spectrum in high yield by culturing a mutant fungus of the genus Aspergillus under aerobic conditions. The process is carried out by (a) isolating a wild strain of the genus Aspergillus which produces acid stable protease;

(b) mutating the wild strain, preferably by UV irradiation;

(c) isolating mutants having protease forming ability of more than 15 mTU/ml by a selection process involving spreading each mutant on a caseinate agar plate, adding a carboxyl protease inhibitor, preferably pepstatin, to the agar medium, incubating the resulting agar plate for a few days, and isolating the mutant colonies with intensified caseinolytic aura formation;

(d) growing these isolated mutants in a nutrient medium containing assimilable carbon and nitrogen sources, at a pH in the range between 3 and 7 and at a temperature between 25° and 50° C.; and (e) separating the resulting protease.

Within the scope of the invention are mutants of the above wild strain which has the depository designation AP 114 (CBS 319.81) insofar as such mutants produce in agitated cultures and under the conditions indicated below, a proteolytic activity of more than 15 mTU/ml and insofar as the resulting protease, on the basis of the test described below (Isoelectrofocussing and immunologic testing) is idential to that of the wild strain. The invention relates in particular to the following mutants:

*Aspergillus niger* AP 114 - III - 69 (CBS 320.81)
*Aspergillus niger* AP 114 - IV - 70 (CBS 321.81)
*Aspergillus niger* AP 114 - IV - 74 (CBS 322.81)
*Aspergillus niger* AP 114 - IV - 80 (CBS 323.81).

The above mutants have been deposited in the Centraal Bureau voor Schimmel-Cultures in Baarn (the Netherlands), and the CBS numbers refer to the depository numbers therein. The isolation of the above mutants was effected in the following manner:

Six-day old slant cultures of the wild strain CBS 319.81 that had formed spores on brewers wort broth agar were eluted with sterile 0.005% sodium lauryl sulfate solution, the spore suspension was filtered through a sterile glass sieve (D-3) to separate the mycelium fragments and then centrifuged for 15 minutes at 6000 rpm. The sedimented spores were taken up in sterile 0.1 M acetate buffer (pH 4.5) and the spore concentration was adjusted under the microscope to about $10^8$ spores/ml. The adjusted spore solution was then irradiated with a UV lamp (wave length 254 nm, 13 watt), until a kill factor of 99.9% was reached. Isolation of active mutant strains was accomplished by spreading the irradiated spores on caseinate agar plates of the following composition:

0.10% Soybean flour
0.10% Corn steepwater
0.50% Casein
0.20% Gelatin
0.24% $KH_2PO_4$
0.10% $MgCl_2.6H_2O$
0.05% $MnSO_4.4H_2O$
0.02% $CaCl_2.2H_2O$
0.04% Sodium desoxycholate
1.00% Glucose
1.60% Agar
pH 5.5
Balance Water In order to permit immediate identification of mutant strains with clearly enhanced protease forming ability, the protease inhibitor, pepstatin, was added to the agar medium at a concentration of 12.5 g/ml. Carboxyl protease inhibitors, other than pepstatin, may also be added. The composition of the caseinate agar medium is also not critical.

The plates were incubated for 3–4 days at 30° C. until the individual spores had grown into defined colonies. Only colonies with enhanced caseinolytic aura formation were then isolated as strain cultures and further tested. The selection criteria for isolating efficient mutant strains were further sharpened by the addition of the protease inhibitor, thereby guaranteeing that only strains with significantly enhanced protease forming ability were selected. The new strains were cultured in agitated cultures at 30° C. to evaluate their proteolytic activity (500 ml Erlenmeyer flask with baffles, agitation frequency 150 rpm). The composition of the medium was as follows:

0.30% Soybean flour
0.30% Corn steepwater
1.00% Gelatin
1.50% Casein
0.24% $KH_2PO_4$
0.10% $MgSO_4.7H_2O$
0.05% $MnCl_2.4H_2O$
0.02% $CaCl_2.2H_2O$
1.0% Corn starch (amylolysis)
pH 5.5
Balance Water In this manner, mutant strains with higher protease activity were isolated from the wild strain. Further mutation experiments were undertaken with the most active of these strains and here again an increase in protease synthesizing performance was produced. The mutation sequences were carried out a total of three times and the following strains were isolated thereby.

TABLE 1

| Strains | Protease Formation (mTU/ml)AP 114 |
| --- | --- |
| AP 114 - III - 69 (CBS 320.81) | 16.0 |
| AP 114 - IV - 70 (CBS 321.81) | 27.7 |
| AP 114 - IV - 74 (CBS 322.81) | 21.4 |
| AP 114 - IV - 80 (CBS 323.81) | 21.6 |
| Aspergillus niger AP 114 (CBS 319.81) var. tienhem (wild strain) | 8.0 |

The protease produced by the mutant strains set forth in Table 1 has the same properties as that of the wild strain CBS 319.81. This protease is characterized by a particularly broad activity spectrum in the weakly acid region between a pH of 2.5 and a pH of 6.5. The optimum activity is at pH 4.5, with the range of 80% maximum activity from a pH of 3.0 to a pH of 6.4.

The protease forming ability of other protease producing *Aspergillus genera*, such as *Aspergillus phoenicii* (ATCC 14332), *Aspergillus awamori* (ATCC 14333), *Aspergillus foetidus* (ATCC 14334), *Aspergillus awamori* (ATCC 14335) or *Aspergillus niger* var. macro (ATCC 16513), can also be enhanced by this novel mutation and selection process.

The following experiments were carried out with the abovementioned Aspergillus strains:

(1) Determination of protease production in agitation flasks, using the medium disclosed above for culturing the new mutants of the invention. The results are given in Table 2.

TABLE 2

| | Strains | | Protease Formation (mTU/ml) |
| --- | --- | --- | --- |
| 1. | Aspergillus phoenicii | ATCC 14322 | 9.0 |
| 2. | Aspergillus awamori | ATCC 14333 | 9.8 |
| 3. | Aspergillus foetidus | ATCC 14334 | 0.5 |
| 4. | Aspergillus awamori | ATCC 14335 | 13.1 |
| 5. | Aspergillus niger var. macro | ATCC 16513 | 7.2 |

(2) Characterization by Isoelectrofocussing (see Example 4).

These tests indicated that the above strains exhibited practically the same extracellular protein spectrum and protease spectrum as *Aspergillus niger* AP 114 (CBS 319.81) and its mutants.

(3) Characterization by the immunologic method (see Example 4).

The strain *Aspergillus niger* AP 114 (CBS 319.81) and its high performance mutants gave cross-reactions with all proteases of the abovementioned Aspergillus strains, but not with proteases of other biological origin.

The protease produced in accordance with the process of the invention is particularly suitable for use as a feed additive, especially to improve the results of raising and fattening poultry, pigs, calves, and commercially raised fish. Moreover, it can also be employed for other purposes where acid stable proteases can be used, such as in the food processing industry; in acid detergents and cleaners, especially in cleaners for tiles, floors and tables, in hospitals and in households; as an aid in tanning leather; and in a highly purified form as a digestive in medical applications.

The process for the production of this protease can be carried out by growing the selected mutants in a liquid or solid nutrient medium, but the liquid nutrient medium is generally preferred. When culturing in a nutrient solution, the usual procedures of aerobic agitation culturing or fermentation are followed.

The nutrient medium to be used in accordance with the invention is prepared by conventional means and should contain a carbon source, a nitrogen source and other nutrients and growth substances needed by the organism. Suitable carbon sources include starch, dextrin, sucrose, glucose, fructose, maltose and sugar-containing waste materials. Suitable nitrogen sources include ammonium salts, urea, casein, gelatin, corn steepwater and soybean flour or soybean cakes. Furthermore, inorganic salts, such as sodium hydrogen phosphate, potassium hydrogen phosphate, ammonium hydrogen phosphate, calcium and magnesium salts may be added to the nutrient medium. Furthermore, it may be advantageous to add growth-promoting substances, such as yeast extract and vitamins, to the nitrient medium.

The fermentation temperature may fluctuate between about 25° C. and about 50° C., but should preferably be between about 27° C. and about 32° C. The pH of the nutrient medium may be between about 3.0 and about 7.0, preferably between about 4.0 and about 6.0. Generally, culturing is carried out over a period of 20 to 96 hours.

The protease produced in accordance with the process of the invention can be precipitated and concentrated from the filtered or centrifuged nutrient solution by conventional methods through the addition of organic solvents or through salting out with, e.g., sodium sulfate or ammonium sulfate. The protease can be purified by dialysis or by treatment with ion exchange resins.

The proteolytic activity of the above protease was determined according to the known method of determination developed by Anson, i.e., dilute quantity of enzyme solution was incubated at 40° C. for 20 minutes with an equal volume of a 1.2% casein solution, which contained 0.6% lactic acid, 6 moles of urea and 0.1 mole of citric or acetic acid. The pH of the casein solution was adjusted to 4.5 by adding 2 N caustic soda solution. After the incubation, 0.4 N trichloroacetic acid was added in a 1:1 volume ratio. The precipitate formed was filtered off from the undigested casein, and the protein fragments in the filtrate formed during the decomposition were determined according to any known protein determination method. Suitable, e.g., is the procedure described by Layne in Methods of Enzymology 3 (1957), pages 448 et seq.

For each determination, a blank must be run by first adding trichloroacetic acid and then the casein solution. This blank, when compared to the reagent standard, indicates that portion of low molecular peptides which was already present in the enzyme solution before the digestion. The difference between the principal and blank values is compared in the indicated method with the extinction which a known amount of tyrosine supplies in this determination. This amount of tyrosine is then a measure for the proteolytic activity of the foregoing enzyme: an enzyme unit (TU) is that amount of enzyme which causes the same extinction difference between the principal and blank values per minute as a 1 M tyrosine solution which is used instead of the enzyme solution.

The measurement of the proteolytic activity at pH values higher and lower than 4.5 can be done without difficulty by suitable adjustment of the casein solution, but in this case the acetic acid is preferably replaced by citric acid.

The following examples are given for illustration purposes only and not to limit the invention.

EXAMPLE 1

In preparing a nutrient medium, 3 g of soybean flour, 3 g of corn steepwater, 15 g of casein, 7 g of gelatin, 2.4 g of $KH_2PO_4$, 0.5 g of $MgSO_4.7H_2O$, 0.1 g of $MnCl_2.4H_2O$, 0.1 g of $CaCl_2.2H_2O$ and 20 g of cornstarch were dissolved or dispersed in 1 liter of water. The pH of the nutrient solution was 5.3. The cornstarch was largely broken down by amylase. The sterilized nutrient solution was inoculated with spores of the mutant CBS 320.81 and the culture was grown in an agitation incubator under optimal aeration at 30° C. for about 50 hours. After this time, the fungus mycelium was filtered off and the mycelium-free culture broth was used for the determination of protease activity in accordance with the above described process. It was found that the culture solution attained an enzymatic activity of 16.0 mTU/ml.

EXAMPLE 2

In preparing the nutrient medium, 10 g of soybean flour (oil-free), 5 g of corn steepwater, 12 g of casein, 5 g of gelatin, 5 g of dry grain slop, 2.4 g of $KH_2PO_4$, 1 g of $NaNO_3$, 1 g of $NH_4Cl$, 0.01 g of $FeSO_4$ and 30 g of native cornstarch were dissolved or dispersed in one liter of tap water. The pH of the nutrient solution was adjusted to 5.3 after autoclaving. 10 ml of a Czapek-Dox preliminary culture (with 5% starch and 0.5% yeast extract) was added to a 1 liter Erlenmeyer flask charged with the above nutrient solution; this nutrient solution was inoculated with the spores of the mutant CBS 321.81 and agitated for 24 hours at 30° C., and aerated at 30° C. for about 72–96 hours, until the pH increased to 6.8–7.0. The mycelium was then filtered off and the clear culture broth used for the determination of protease activity according to the above-described procedure. It was found that the culture solution attained an enzymatic activity of 27.7 mTU/ml. The protease was isolated by clarification/filtration of the broth contained in 10–1 liter agitation flasks after adding 5 g of Filter Cel and 5 g of standard Super Cel from Mansfield Corp., compressed at 50 Torr to one third of the initial volume, and precipitated by adding 39% of anhydrous sodium sulfate with agitation, whereby the temperature increased to 38°–40° C. Alternatively, the protease may be precipitated by dropwise addition of 2 volumes of ethanol, methanol, acetone, or other water-miscible solvents at a temperature of $-3°$ C. to 5° C. The precipitate was removed and dried under vacuum.

EXAMPLE 3

Using the above described determination process, the activity of the protease isolated in accordance with Examples 1 and 2 was determined in relation to the pH. Table 3 contains the pH range for the optimum activity and for 50% of optimum activity measured at the optimum pH range. The values indicate that the proteases of mutants used in Examples 1 and 2 have the same favorable broad pH activity spectrum for the above-mentioned applications as the protease isolated from the wild form CBS 319.81.

TABLE 3

| Enzyme | pH for optimum activity | pH for 50% of optimum activity |
|---|---|---|
| Protease from Mutant CBS 320.81 | 4.0–4.5 | 2.5–6.5 |
| Protease from Mutant CBS 321.81 | 4.0–4.5 | 2.5–6.5 |
| Protease from CBS 319.81 (wild form) | 4.0–4.5 | 2.5–6.5 |

EXAMPLE 4

The proteases obtained from the mutants CBS 320.81, CBS 321.81, CBS 322.81, and CBS 323.81 were compared by the method of Isoelectrofocussing or cross-reaction of Ouchterlony with the protease obtained from the wild strain CBS 319.81. In this manner, the complete identity of all proteases was established.

Description of the method of isoelectrofocussing

Equipment: Multiphor 2117, LKB Instruments LKB 2103 Power Supply
Material: LKB Ampholine PAG plates, LKB Instruments pH 3.5–9.5
Anode solution: 1 M $H_3PO_4$
Cathode solution: 1 M NaOH Isoelectrofocussing After application of polyacrylamide gel to the water-cooled apparatus, the electrode solution soaked paper electrode strips were placed on the border of the gel. 5 mm wide filter strips were placed on the center line of the gel between the anode and the cathode and 10 μl of a salt-free test solution (5 mg/ml protein) was added dropwise. After the apparatus was closed, the pH gradient was built up to a current intensity of 10 mA, the test filter strips were removed after 30 minutes and the current intensity increased to 15 mA. The separation was completed after 2 to 2.5 hours.

Determination of the pH gradients

The pH gradient was determined with a calibrated surface pH electrode so as to provide readings of pH fluctuations between the anode and the cathode at several lines; a pH/cm diagram was constructed therefrom.

Fixing and staining

Fixing solution: Distilled water was added to 57.5 g of trichloroacetic acid and 17.25 g of sulfosalicylic acid and the solution was completed to 500 ml.
Destaining: A mixture of 500 ml of ethanol and 160 ml of acetic acid was diluted with distilled water to 2000 ml.
Staining solution: 0.46 g of Coomassie Blue G-250 in 400 ml of destaining solution.

After construction of the pH profile, the gel was left for one hour in an agitated fixing solution to achieve protein precipitation and Ampholine removal, then washed for 5 minutes with destaining solution, followed by 10 minutes in staining solution at 60° C. The gel was destained by changing the destaining solution several times until the blue colored protein strips were clearly brought out from the background.

The isoelectric points of the proteins were determined by means of the pH profile.

Description of the method of cross-reaction according to Ouchterlony

Material

Immunodiffusion plates (Code No. 64-276-1) made by Miles, Frankfurt, were used for the cross-reaction. The pre-prepared flasks contain 0.9% agarose in a borate/sodium chloride buffer, pH 7.5, ionic strength 0.175%. In addition, the plates contain 0.01% thiomersal as a bacteriostatic and trypan blue as an indicator for the protein precipitation lines.

Protease CBS 319.81 antibodies were obtained from rabbits.

Protease CBS 319.81 served as a positive control for immunization.

Procedure

25 μl of antiserum was pipetted into the middle of the diffusion plates and 25 μl of protease solution in a concentration of 5 mg/ml or 10 mg/ml was pipetted into each of the external holes.

Diffusion time: 72 hours at 4° C.

The precipitation lines may be detected by means of the trypan blue indicator in the agarose. The immunological cross-reaction is then only positive if the antibody producing protease is identical to the tested protease. This is ascertained by blending of the precipitation lines.

TABLE 5

| Protease | Cross-reaction versus AP 114 antibodies | Cross-reaction versus SP 1 antibodies |
|---|---|---|
| 1. Aspergillus phoenicii ATCC 14332 | + | − |
| 2. Aspergillus awamori ATCC 14333 | + | − |
| 3. Aspergillus foetidus ATCC 14334 | + | − |
| 4. Aspergillus awamori ATCC 14335 | + | − |
| 5. Aspergillus niger ATCC 16513 var. macro | + | − |
| 6. AP 114 - III - 69 (CBS 320.81) | + | − |
| 7. AP 114 - IV - 70 (CBS 321.81) | + | − |
| 8. AP 114 - IV - 74 (CBS 322.81) | + | − |
| 9. AP 114 - IV - 80 (CBS 323.81) | + | − |
| 10. Aspergillus niger AP 114 var. tienhem (CBS 319.81) | + | − |

What is claimed is:

1. A mutant form of the wild fungus strain *Aspergillus niger* var. tienhem CBS 319.81 selected from the group consisting of mutants having the following depository designations:
Aspergillus niger AP 114 - III - 69 (CBS 320.81)
Aspergillus niger AP 114 - IV - 70 (CBS 321.81)
Aspergillus niger AP 114 - IV - 74 (CBS 322.81)
Aspergillus niger AP 114 - IV - 80 (CBS 323.81).

* * * * *

TABLE 4

Results of isoelectric focussing

| PI-value | ATCC 14332 | | ATCC 14333 | | ATCC 14334 | | ATCC 14335 | | ATCC 16513 | | CBS 320.81 | | CBS 321.81 | | CBS 322.81 | | CBS 323.81 | | CBS 319.81 | |
|---|---|---|---|---|---|---|---|---|---|---|---|---|---|---|---|---|---|---|---|---|
| | a | b | a | b | a | b | a | b | a | b | a | b | a | b | a | b | a | b | a | b |
| 3.5 | xxxx | — | xxxx | xx | xxxx | xx | xxxx | xx | xxxx | x | xxxx | xxx | xxxx | xx | xxxx | xx | xxxx | xx | xxxx | xx |
| 3.7 | x | — | xx | xx | xx | xx | xx | xx | — | — | xx | x | xx | xx | xx | xx | xx | xx | xx | xx |
| 3.95 | x | — | — | — | — | — | — | — | — | — | — | — | — | — | — | — | — | — | — | — |
| 4.0 | x | xxxx | xxxx | xxxx | xxxx | xxxx | xxxx | xxxx | xxx | xxx | xxxx | xxxx | xxxx | xxxx | xxxx | xxxx | xxxx | xxxx | xxxx | xxxx |
| 4.05 | x | — | x | — | x | — | x | — | — | — | x | — | x | — | x | — | x | — | x | — |
| 4.3 | x | — | x | — | x | — | x | — | — | — | x | — | x | — | x | — | x | — | x | — |
| 4.6 | x | — | x | — | x | — | x | — | — | — | — | — | x | — | x | — | x | — | x | — | a Coomassie blue (= Protein)
b Zymogramm (= Protease)